United States Patent
During

(10) Patent No.: US 11,130,952 B2
(45) Date of Patent: *Sep. 28, 2021

(54) USE OF MIR-92A OR MIR-145 IN THE TREATMENT OF ANGELMAN SYNDROME

(71) Applicant: Ovid Therapeutics Inc., New York, NY (US)

(72) Inventor: Matthew During, Weston, CT (US)

(73) Assignee: Ovid Therapeutics Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/922,273

(22) Filed: Jul. 7, 2020

(65) Prior Publication Data

US 2020/0332294 A1 Oct. 22, 2020

Related U.S. Application Data

(63) Continuation of application No. 16/441,391, filed on Jun. 14, 2019, now Pat. No. 10,704,048.

(60) Provisional application No. 62/684,774, filed on Jun. 14, 2018.

(51) Int. Cl.
*A61K 48/00* (2006.01)
*C07H 21/02* (2006.01)
*C12N 15/113* (2010.01)

(52) U.S. Cl.
CPC ...... *C12N 15/113* (2013.01); *C12N 2310/141* (2013.01); *C12N 2320/32* (2013.01)

(58) Field of Classification Search
CPC .................... C12N 2310/141; C12N 15/113
See application file for complete search history.

(56) References Cited

U.S. PATENT DOCUMENTS

| | | | |
|---|---|---|---|
| 5,752,515 | A | 5/1998 | Jolesz et al. |
| 9,617,539 | B2 | 4/2017 | Rigo et al. |
| 10,704,048 | B2 | 7/2020 | During |
| 2009/0005711 | A1 | 1/2009 | Konofagou et al. |
| 2015/0152410 | A1 | 6/2015 | Krieg et al. |
| 2018/0098974 | A1 | 4/2018 | During |
| 2018/0104358 | A1 | 4/2018 | Nash et al. |
| 2019/0298843 | A1 | 10/2019 | Low |

FOREIGN PATENT DOCUMENTS

WO 2006128245 A1 12/2006

OTHER PUBLICATIONS

Gagnon et al., "RNAi Factors are Present and Active in Human Cell Nuclei," Cell Rep., Jan. 16, 2015, vol. 16, No. 1;pp. 211-221.
Grier et al., "Toward a Broader View of Ube3a in a Mouse Model of Angelman Syndrome: Expression in Brain, Spinal Cord, Sciatic Nerve and Glial Cells," PLOS One, Apr. 20, 2015; pp. 1-14.
Khudayberdiev et al., "A comprehensive characterization of the nuclear microRNA repertoire of post-mitotic neurons," Frontiers in Molecular Neuroscience, , vol. 6, Article 43; Nov. 26, 2013; pp. 1-19.
FAST News, About GeneTx, dated Feb. 22, 2018; 2 pages.
Wang et al., The long non-coding RNA SNHG14 inhibits cell proliferation and invastion and promotes apoptosis by sponging miR-92a-3p in glioma, Oncotarget, 2018, vol. 9, No. 15; pp. 12112-12124.
Qi et al., Long Non-Coding RNA SNHG14 Promotes Microglia Activation by Regulating MIR-145-5P/PLA2G4A in Cerebral Infaction, Neuroscience, 348, (2017); pp. 98-106.
Robb et al., "Specific and potent RNAi in the nucleus of human cells," Nature Structural & Molecular Biology, Feb. 2005, vol. 12, No. 2, pp. 133-137.
Ohrt et al., "siRNA Modifications and Sub-Cellular Localization: A Question of Intracellular Transport," Current Pharmaceutical Design, 2008, vol. 14, No. 34; pp. 3674-3685.
Hynyen et all., Local and reversible blood-brain barrier disruption by noninvasive focused ultrasound at frequencies suitable for trans-skull sonications, NeuroImage, 2005, vol. 24; pp. 12-20.
Albrecht et al., "Imprinted expression of the murine Angelman syndrome gene, Ube3a, in hippocampal and Purkinje neurons," Nature Genetics, Sep. 1997, vol. 17; pp. 75-78.
Charbel et al., "Assessment of Tropism and Effectiveness of New Primate-Derived Hybrid Recombinant AAV Serotypes in the Mouse and Primate Retina," PLOS One, Apr. 2013, vol. 8, Issue 4; pp. 1-12 (e60361).
International Search Report and Written Opinion of the International Searching Authority, dated Sep. 16, 2019, corresponding to counterpart International Application No. PCT/US19/37174; 10 pages.
Meng et al., "Towards a therapy for Angelman syndrome by reduction of a long non-coding RNA," Nature, vol. 518, No. 7539, Feb. 19, 2015; pp. 409-412.
Speranza et al., "NEDD9, a novel target of miR-145, increases the invasiveness of glioblastoma," Oncotarget, vol. 3, No. 7, May 2012; pp. 723-734.
Ibrahim et al., "MicroRNA Replacement THerapy for miR-145 and miR-33a Is Efficacious in a Model of Colon Carcinoma," Cancer Research, vol. 71, No. 15, Aug. 1, 2011; pp. 5214-5224.

*Primary Examiner* — Amy H Bowman
(74) *Attorney, Agent, or Firm* — Carter, DeLuca & Farrell LLP

(57) ABSTRACT

Expression of micoRNAs that negatively regulate the activity of the SNHG14 gene for can be used in treatment of Angelman Syndrome. Such microRNAs include, for example, MIR-92a and/or MIR-145, as well as analogues and variants thereof, for use in treatment of Angelman Syndrome. Expression vectors such as, for example, AAV vectors may be used to transduce cells for introduction of MIR-92a and/or MIR-145 into target tissues for treatment of Angelman Syndrome.

11 Claims, No Drawings
Specification includes a Sequence Listing.

SEQUENCE LISTING

<160> NUMBER OF SEQ ID NOS: 2

<210> SEQ ID NO 1
<211> LENGTH: 22
<212> TYPE: RNA
<213> ORGANISM: Artificial Sequence
<220> FEATURE:
<223> OTHER INFORMATION: Synthetic: microRNA-92a-3p

<400> SEQUENCE: 1
uauugcacuu gucccggccu gu                                                22

<210> SEQ ID NO 2
<211> LENGTH: 23
<212> TYPE: RNA
<213> ORGANISM: Artificial Sequence
<220> FEATURE:
<223> OTHER INFORMATION: Synthetic: microRNA-145-5p

<400> SEQUENCE: 2
guccaguuuu cccaggaauc ccu                                               23

USE OF MIR-92A OR MIR-145 IN THE TREATMENT OF ANGELMAN SYNDROME

CROSS-REFERENCE TO RELATED APPLICATION

This application is a continuation application of U.S. patent application Ser. No. 16/441,391, filed Jun. 14, 2019, now U.S. Pat. No. 10/704,048, which claims benefit and priority to U.S. Provisional Application No. 62/684,774, filed Jun. 14, 2018, which are incorporated herein by reference in their entireties.

TECHNICAL FIELD

The present disclosure relates generally to expression of micoRNAs that negatively regulate the activity of the SNHG14 gene for use in treatment of Angelman Syndrome. Such microRNAs include, for example, MIR-92a and/or MIR-145, as well as analogues and variants thereof, for use in treatment of Angelman Syndrome. More specifically, the present disclosure relates to the use of expression vectors such as, for example, AAV vectors that may be used to transduce cells for introduction of MIR-92a and/or MIR-145 into the target tissues for treatment of Angelman Syndrome.

BACKGROUND

"Angelman syndrome" (AS) is a neurodevelopmental disorder characterized by severe developmental delay or intellectual disability, severe speech impairment, gait ataxia and/or tremulousness of the limbs, seizures, microcephaly and a unique behavior with an inappropriate happy demeanor that includes frequent laughing, affinity for water, smiling, and excitability. Microcephaly and seizures are also common. Developmental delays are first noted at around age six months; however, the unique clinical features of Angelman syndrome do not become manifest until after age one year, and it can take several years before the correct clinical diagnosis is obvious.

Many of the characteristic features of Angelman syndrome result from the loss of function of a gene called UBE3A which encodes for ubiquitin protein ligase E3A (UBE3A) gene. (Kishino, T. et al. Nat Genet (1997) 12:385-395). People normally inherit one copy of the UBE3A gene from each parent. Both copies of this gene are turned on (active) in many of the body's tissues, however, in certain areas of the brain, only the copy inherited from a person's mother (the maternal copy) is active. This parent-specific gene activation is caused by a phenomenon called genomic imprinting. UBE3A is maternally imprinted in the brain, such that it is expressed nearly exclusively from the maternal chromosome while the paternal chromosome is epigenetically silenced. (Albrecht, U. et al., Nat Genet (1997) 17:75-78). If the maternal copy of the UBE3A gene is lost because of a chromosomal change or a gene mutation, a person will have no active copies of the gene in some parts of the brain.

Several different genetic mechanisms can inactivate or delete the maternal copy of the UBE3A gene. Most cases of Angelman syndrome (about 70 percent) occur when a segment of the maternal chromosome 15 containing this gene is deleted. In other cases (about 11 percent), Angelman syndrome is caused by a mutation in the maternal copy of the UBE3A gene.

Small nucleolar RNA host gene 14 (SNHG14), alternatively known as UBE3A-ATS, extends antisense into the UBE3A gene and thus plays a potential role in suppression of paternal UBE3A expression and imprinting. Much remains to be understood regarding how insufficiency of the protein product of UBE3A results in the observed neurodevelopmental deficits observed in Angelman Syndrome. Accordingly, there remains a need for improved and/or additional therapies for treating subjects diagnosed with Angelman Syndrome.

SUMMARY

A method of treating Angelman Syndrome (AS) in a patient in need thereof is provided which includes delivering to the patient an effective amount of a composition that negatively regulates the activity of the SNHG14 gene. Such methods of treatment include delivery to a patient an effective amount of a composition that increases the level of microRNA-145 and/or microRNA-92a molecules in the central nervous system of the patient. The method disclosed herein is designed to negatively regulate the activity of the SNHG14 gene.

A method of treating Angelman Syndrome in a patient in need thereof is provided which includes delivering to the patient an effective amount of a composition that increases the level of microRNA-145 and/or microRNA-92a molecules in cells of the central nervous system of the patient. A method of treating Angelman Syndrome in a patient in need thereof is provided which includes administering a vector encoding microRNA-145, pri-miRNA145 or pre-miRNA145 to the patient. A method of treating Angelman Syndrome in a patient in need thereof is provided which includes administering a vector encoding microRNA-92a, pri-miR92a or pre-miRNA92a. In embodiments, increased levels of microRNA-145 or microRNA-92a cause improvement in one or more symptoms of the Angelman Syndrome.

In embodiments, a vector encoding microRNA-145, pri-miR145 or pre-miR145, causes increased levels of microRNA-145 in a patient with Angelman Syndrome and is associated with reduced symptoms of the disorder. In embodiments, a vector encoding microRNA-92a, pri-miR92a or pre-miR92a causes increased levels of microRNA-92a in a patient with Angelman Syndrome and is associated with reduced symptoms of the disorder.

In certain aspects, a vector including nucleic acids encoding microRNA-145, pri-miR145 or pre-miR145, includes a promoter operatively linked to the nucleic acid encoding microRNA-145, pri-miR145 or pre-miR145. In embodiments, the vector includes a woodchuck post-transcriptional regulatory element (WPRE). In embodiments, the vector includes a bovine growth hormone polyadenylation sequence (BGHpA). In embodiments, the vector includes a fluorescence reporter cassette. In embodiments, the vector is an adeno-associated virus. In embodiments, the vector is a lentivirus. In embodiments, a vector including nucleic acid encoding microRNA-92a, pri-miR92a or pre-miR92a, includes a promoter operatively linked to the nucleic acid encoding microRNA-92a, pri-miR92a or pre-miR92a. In embodiments, the nucleic acid encoding microRNA-92a is microRNA-92a-3p. In embodiments, the vector includes a woodchuck post-transcriptional regulatory element (WPRE). In embodiments, the vector includes a bovine growth hormone polyadenylation sequence (BGHpA). In embodiments, the vector includes a fluorescence reporter cassette. In embodiments, the vector is an adeno-associated virus. In embodiments, the vector is a lentivirus. In embodiments, the vector is an AAV vector.

In embodiments, the vector is delivered to a target location in the patient's central nervous system. In embodiments, the target location is the patient's brain. In embodiments, the route of administration of the vector is oral, buccal, sublingual, rectal, topical, intranasal, vaginal or parenteral. In embodiments, the vector is administered directly to the target location.

In embodiments, ultrasound is applied to a target location in the patient's brain to enhance permeability of the patient's blood brain barrier at a target location, wherein microRNA-145 or microRNA-92a is delivered to the target location.

DETAILED DESCRIPTION

Described herein are methods and compositions for treating Angelman Syndrome which include administering compositions that negatively regulate the activity of the SNGH14 gene. Such compositions include, for example, microRNA-145, pri-miR145 or pre-miR145, to a patient having Angelman Syndrome. Also described herein are methods and compositions for treating Angelman Syndrome which include administering microRNA-92a, pri-miR92a or pre-miR92a, to a patient having Angelman Syndrome.

In embodiments, vectors encoding microRNA-145, pri-miR145 or pre-miR145 are provided. In embodiments, vectors encoding microRNA-145, pri-miR145 or pre-miR145 are administered to a patient having Angelman Syndrome wherein the patient exhibits improvement in one or more symptoms of the disorder. In embodiments, vectors encoding microRNA-92a, pri-miR92a or pre-miR92a are provided. In embodiments, vectors encoding microRNA-92a, pri-miR92a or pre-miR92a are administered to a patient having Angelman Syndrome wherein the patient exhibits improvement in one or more symptoms of the disorder.

MicroRNA-145, pri-miR145, pre-miR145, microRNA-92a, pri-miR92a, and/or pre-miR92a, are collectively referred to herein as microRNA or microRNAs. Administration to a patient of microRNA-145, pri-miR145, pre-miR145, microRNA-92a, pri-miR92a, and/or pre-miR92a, is collectively referred to herein as microRNA treatment. MicroRNA treatment increases the level of respective active microRNA molecules in a cell. The increase can come about by directly providing the microRNA to a cell, or may come about by indirectly providing microRNA to cell, such as through a vector. The microRNA may include a RNA or DNA molecule that also includes additional sequences. Increases in the level of respective active microRNA molecules in cells of the CNS, for example, the brain of a patient are associated with an improvement in one or more symptoms of Angelman Syndrome.

One or more pri-miRNA(s) can be used in the compositions and methods described herein. Any suitable form of a pri-mRNA can be used. The pri-mRNA(s) can be processed intracellularly and act to gain function for the miRNA, e.g., converted into pre-mRNA(s) and then the mature form. Alternatively, the miRNA may initially be a miRNA precursor. In embodiments, the compositions and methods include pre-miRNA, which is subject to cleavage by an RNAse III type double stranded endonuclease called Dicer, resulting in an imperfect miRNA:miRNA* duplex that is about 20-25 nucleotides in size. This duplex contains the mature miRNA strand and its opposite complementary miRNA* strand. One or more pre-miRNA(s) can be used in the compositions and methods described herein. The pre-miRNA may act to gain function for the miRNA. Any suitable form of a pre-miRNA can be used. It is also contemplated that the miRNA of the compositions and methods described herein may be mature miRNA.

The microRNAs can be delivered to cells in non-expression vector or expression vector modalities. Expression vector and vector are used interchangeably herein. In embodiments, microRNA may be isolated or purified prior to use in a subsequent step. MicroRNAs may be isolated or purified prior to introduction into a cell. "Introduction" into a cell includes known methods of transfection, transduction, infection and other methods for introducing an expression vector or a heterologous nucleic acid into a cell. A template nucleic acid or amplification primer may be isolated or purified prior to it being transcribed or amplified. Isolation or purification can be performed by a number of methods known to those of skill in the art with respect to nucleic acids. The delivery of the microRNA may occur through several forms, such as through encapsulation of a chemically modified or through an unmodified RNA moiety within a viral or non-viral delivery vessel. Non-expression vector delivery modalities include nanoparticles, microparticles, liposomes, polymers, microspheres, etc., which may be targeted to brain cells. The microRNA can also be delivered as a plasmid or mini-vector based expression system where it can then be expressed and processed by the RNAi machinery in cells to form a mature microRNA.

Nucleic acid constructs for miRNA expression may be produced recombinantly. Such expression vectors are provided herein. Expression vectors are a carrier nucleic acid into which a nucleic acid sequence can be inserted for introduction into a cell where it can be replicated. Expression vectors include plasmids, cosmids, recombinant viruses, such as adeno-associated virus (AAV), adenoviruses, retroviruses, poxviruses, and other known viruses in the art (bacteriophage, animal viruses, and plant viruses), and artificial chromosomes (e.g., YACs). A person of ordinary skill in the art is well equipped to construct expression vectors through standard recombinant techniques. In embodiments, an expression vector having a microRNA is delivered to cells of a patient. The nucleic acid molecules are delivered to the cells of a patient in a form in which they can be taken up and are advantageously expressed so that therapeutically effective levels can be achieved.

Nucleic acid molecules for use in the vectors disclosed herein include those encoding for mammalian microRNA-145, pri-miR145, pre-miR145, microRNA-92a, pri-miR92a, or pre-miR92a. Such nucleic acids are well known in the art and publically available. In an embodiment of the invention, human microRNA-145, pri-miR145, pre-miR145, microRNA-92a, pri-miR92a, or pre-miR92a sequences are used in the vectors. The mature sequence for human microRNA-92a, also referred to as microRNA-92a-3p is:

(SEQ ID NO: 1) 5'-UAUUGCACUUGUCCCGGC-CUGU-3'

The mature sequence for human microRNA-145, also referrred to as microRNA-145-5p is: (SEQ ID NO: 2) 5'GUCCAGUUUUCCCAGGAAUCCCU-3'

In addition to wild type microRNA-145 and microRNA-92a encoding nucleic acids, variants of said nucleic acids may also be used in the methods of the invention. Such variants may, for example, affect the localization of the microRNA within the cell. Such variants may result in a reduction in the nuclear localization of the microRNA with an increase in cytoplasmic localization. In an aspect of the invention, microRNA-145 and microRNA-92a mimics may also be used to treat Angelman Syndrome. Such mimics are commercially available (See, Sigma Aldrich, for example).

Any suitable expression vector known to those skilled in the art may be utilized to deliver microRNA(s) herein to a target location in cells of the central nervous system. Upon such delivery, cells in the target locations are transfected with microRNA(s), thereby increasing levels of those microRNA(s) in the brain of the patient. Transducing viral (e.g., retroviral, adenoviral, lentiviral and adeno-associated viral) vectors can be used for somatic cell gene therapy, especially because of their high efficiency of infection and stable integration and expression.

In embodiments, the expression vector may be a stable integrating vector or a stable nonintegrating vector. Examples of suitable vectors are lentiviruses and adeno-associated viruses (AAV). Lentiviruses are a subclass of retroviruses. Lentiviruses can integrate into the genome of non-dividing cells such as neurons. Lentiviruses are characterized by high-efficiency infection, long-term stable expression of transgenes and low immunogenicity. In embodiments, lentiviral vectors may be utilized to deliver microRNA(s) to the brain.

AAV is a defective parvovirus known to infect many cell types and is nonpathogenic to humans. AAV can infect both dividing and non-dividing cells. In embodiments, AAV vectors may be utilized herein to deliver microRNA(s) to the brain. Any of the known adeno-associated viruses (AAV) may be utilized herein, e.g., AAV1, AAV2, AAV4, AAV5, AAV8, AAV9 and AAVRec3 may be utilized in connection with neurons. AAV vectors for use in the methods disclosed herein include those described in U.S. Ser. No. U.S. Provisional Patent Application No. 62/550,458 which is incorporated by reference herein in its entirety. Additional suitable AAV serotypes have been developed through pseudotyping, i.e., mixing the capsid and genome from different viral serotypes. Accordingly, e.g., AAV2/7 indicates a virus containing the genome of serotype 2 packaged in the capsid from serotype 7. Other examples are AAV2/5, AAV2/8, AAV2/9, etc. Hybrid AAV capsid serotypes rec1, rec2, rec3 and rec4 were generated by shuffling the fragments of capsid sequences that matched in all three non-human primate AAV serotypes cy5, rh20 and rh39, with AAV8. See, Charbel et al., PLoS One. 2013 Apr. 9;8(4):e60361. The terms rec3AAV and AAVRec3 may be used interchangeably herein. Self-complementary adeno-associated virus (scAAV) may also be utilized as vectors. Whereas AAV packages a single strand of DNA and requires the process of second-strand synthesis, scAAV packages both strands which anneal together to form double stranded DNA. By skipping second strand synthesis scAAV allows for rapid expression in the cell.

Suitable vectors may be constructed by those having ordinary skill in the art using known techniques. Suitable vectors can be chosen or constructed, containing, in addition to microRNA(s), appropriate regulatory sequences, including promoter sequences, terminator fragments, polyadenylation sequences, marker genes and other sequences as appropriate. Those skilled in the art are familiar with appropriate regulatory sequences, including promoter sequences, terminator fragments, polyadenylation sequences, marker genes and other suitable sequences.

Expression vectors herein include appropriate sequences operably linked to the coding sequence or ORF to promote its expression in a targeted host cell. "Operably linked" sequences include both expression control sequences such as promoters that are contiguous with the coding sequences and expression control sequences that act in trans or distally to control the expression of the desired product.

Typically, the vector includes a promoter to facilitate expression of the microRNA(s) within a target cell. The promoter may be selected from a number of constitutive or inducible promoters that can drive expression of the selected transgene in the brain. Examples of constitutive promoters include CMV immediate early enhancer/chicken beta-actin (CBA) promoter-exon 1-intron 1 element, RSV LTR promoter/enhancer, the SV40 promoter, the CMV promoter, dihydrofolate reductase (DHFR) promoter, and the phosphoglycerol kinase (PGK) promoter.

Specificity can be achieved by regional and cell-type specific expression of the receptor exclusively, e.g., using a tissue or region specific promoter. Virus gene promoter elements may help dictate the type of cells that express microRNA(s). Some promoters are nonspecific (e.g., CAG, a synthetic promoter), while others are neuronal-specific. The CAG promoter is a strong synthetic promoter that can be used to drive high levels of expression. The CAG promoter consists of 1) a cytomegalovirus (CMV) early enhancer element, 2) the promoter, the first exon and the first intron of the chicken beta-actin gene, and 3) the splice acceptor of the rabbit beta-globin gene. In embodiments the promoter is the CAG promoter. Neuronal specific promoters include (e.g., synapsin; hSyn), or preferential to specific neuron types, e.g., dynorphin, encephalin, GFAP (Glial fibrillary acidic protein) which is preferential to astrocytes, or CaMKIIa, which is preferential to cortical glutamatergic cells but can also target subcortical GABAergic cells. In embodiments, the promoter is the CamkIIa (alpha CaM kinase II gene) promoter, which may drive expression in the forebrain. Other neuronal cell type-specific promoters include the NSE promoter, tyrosine hydroxylase promoter, myelin basic protein promoter, glial fibrillary acidic protein promoter, and neurofilaments gene (heavy, medium, light) promoters.

Expression control sequences may also include appropriate transcription initiation, termination, and enhancer sequences; efficient RNA processing signals such as splicing and polyadenylation signals; sequences that stabilize cytoplasmic mRNA; sequences that enhance translation efficiency (e.g., Kozak consensus sequence); sequences that enhance nucleic acid or protein stability; and when desired, sequences that enhance product processing and/or secretion. Many varied expression control sequences, including native and non-native, constitutive, inducible and/or tissue-specific, are known in the art and may be utilized herein depending upon the type of expression desired.

In addition to promoters, expression control sequences for eukaryotic cells typically include an enhancer, such as one derived from an immunoglobulin gene, SV40, CMV, etc., and a polyadenylation sequence which may include splice donor and acceptor sites. The polyadenylation sequence generally is inserted 3' to the coding sequence and 5' to the 3' ITR sequence. Illustrative examples of polyA signals that can be used in a vector herein include polyA sequence (e.g., AATAAA, ATTAAA, or AGTAAA), a bovine growth hormone polyA sequence (BGHpA), a rabbit beta-globin polyA sequence (rβgpA), or another suitable heterologous or endogenous polyA sequence known in the art.

Regulatory sequences useful herein may also contain an intron, such as one located between the promoter/enhancer sequence and the coding sequence. One useful intron sequence is derived from SV40, and is referred to as the SV40 T intron sequence. Another includes the woodchuck hepatitis virus post-transcriptional element (WPRE). WPRE is a DNA sequence that, when transcribed, creates a tertiary structure that enhances expression.

Vectors herein may contain reporter genes, e.g., those which encode fluorophores. A fluorophore is a fluorescent compound that can re-emit light upon excitation, usually at specific frequencies. They can be used as a tag or marker which can be attached to, e.g., a protein to allow the protein to be located. Many suitable fluorophores are known in the art. They may be categorized by the color they emit, e.g., blue, cyan, green, yellow, orange, red and others. For example, mCherry, mRasberry, mTomato and mRuby are red fluorophore proteins; citrine, venus, and EYFP are yellow fluorophore proteins. Green fluorescent protein (GFP) is a commonly used fluorophore.

The microRNAs described herein, whether delivered by expression vector or by non-expression vector modalities, are used to treat Angelman Syndrome. Symptoms of Angelman Syndrome may include, but are not limited to intellectual disability, lack of speech, seizures, and a characteristic behavioral profile. The behavioral features of Angelman Syndrome include a happy demeanor, easily provoked laughter, short attention span, hypermotoric behavior, mouthing of objects, sleep disturbance, and an affinity for water. Methods of treatment herein can include providing improvement in one or more of the foregoing symptoms.

In certain aspects, a patient suspected of carrying a genetic defect resulting in Angelman Syndrome may be tested prior to treatment to detect and confirm the presence of such a defect. In one example, the patient may be tested to detect defects in the UBE3A gene. Molecular genetic testing (methylation testing and UBE3A sequence analysis) is capable of identifying alterations in approximately 90% of individuals.

Once a determination has been made of the location of a suspected location of abnormal activity associated with Angelman Syndrome in a patient, targeted treatment in accordance with the present disclosure can be implemented. Methods of determining the location of abnormal activity in the brain, or additionally affected neuronal tissue, are well-known in the art. In embodiments, areas determined to be the site of origin of the abnormal activity can be targeted.

In some embodiments, the vectors disclosed herein are administered directly to the central nervous system, e.g., the brain or the spinal cord. Any method known in the art to administer vectors directly to the central nervous system can be used. The vectors may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes, cortex, basal ganglia, hippocampus and amygdala), limbic system, neocortex, corpus striatum, cerebrum, and inferior colliculus. The vectors may be delivered into the cerebrospinal fluid by, for example, lumbar puncture. In an addition, when administration is performed intravenously, ultrasound may be applied to a target location in the patient's brain to enhance permeability of the patient's blood brain barrier at the target location for uptake of the vectors. The application of ultrasound for enhancing the permeability of the patient's blood brain barrier is disclosed in Ser. No. 62/471,635, the content of which is incorporated herein in its entirety.

Methods for administering materials directly to target locations such as the brain, are well-known. For example, a hole, e.g., Burr hole, can be drilled into the skull and an appropriately sized needle may be used to deliver a vector or non-vector vehicle to a target location. In embodiments, a portion of the skull may be removed to expose the dura matter (craniotomy) at or near a target location and a vector or non-vector vehicle can be administered directly to the target location. In embodiments, a vector or non-vector vehicle is injected intracranially using stereotaxic coordinates, a micropipette and an automated pump for precise delivery of the vector or non-vector vehicle to the desired area with minimal damage to the surrounding tissue.

In certain aspects, a micropump may be utilized to deliver pharmaceutical compositions containing a vector or non-vector vehicle containing the microRNA(s) to target areas in the brain. The compositions can be delivered immediately or over an extended period of time, e.g., over 1, 2, 3, 4, 5, 6, 7, 8, 9, 10 or more minutes. After vector delivery to a target location in the brain a sufficient amount of time may be allowed to pass to allow expression of the microRNA(s) at the target location.

In certain aspects, vectors or nonvector delivery vehicles herein can be administered systemically. Systemic delivery includes oral, buccal, sublingual, rectal, topical, intranasal, vaginal and parenteral modes of administration. Examples of parenteral modes of administration include intravenous, intraperitoneal, intramuscular and subcutaneous modes of administration. In embodiments, vectors or nonvector delivery vehicles will circulate until they contact the target location(s) in the CNS, including the brain, where they deliver the microRNA(s) or cause the microRNA(s) to be expressed and act, e.g., to aid in network formation and/or modulate neuronal signaling networks.

The microRNA(s) is used in an amount effective against Angelman Syndrome in patients. The dosage of the active ingredient depends upon the age, weight, and individual condition of the patient, the individual pharmacokinetic data, and the mode of administration. In the case of an individual human having a bodyweight of about 70 kg the daily dose administered of a microRNA can be from 0.01 mg/kg bodyweight to 100 mg/kg bodyweight, e.g., from 0.1 mg/kg bodyweight to 50 mg/kg bodyweight, from 1 mg/kg to 20 mg/kg bodyweight administered as a single dose or as several doses.

In embodiments, treatment with ultrasound is used to enhance delivery of the microRNA(s) to target locations in the brain by disrupting the blood brain barrier. Use of focused ultrasound energy herein disrupts the BBB without adversely affecting the vector, non-vector delivery vehicle, the microRNA(s), and/or brain tissue itself. Use of ultrasound energy herein can increase the speed of delivery of vectors, non-vector delivery vehicles, and/or the microRNA(s) to target locations in the brain, reduce side effects which may be associated with delivery of vectors non-vector delivery vehicles, and/or the microRNA(s) to target locations in the brain, reduce dosage amounts while concentrating vectors, non-vector delivery vehicles, and/or the microRNA(s) at a target location and can allow controlled release of the amount of vectors, non-vector delivery vehicles, and/or the microRNA(s) at a target location. Methods for delivering ultrasound energy through the skull are known in the art. See, e.g., U.S. Pat. No. 5,752,515 and US Publication No. 2009/0005711, both of which are hereby incorporated by reference in their respective entireties. See also, Hynynen et al., NeuroImage 24 (2005) 12-120.

In accordance with the present disclosure, microRNA treatment provides improvement in one or more symptoms of Angelman Syndrome for more than 1 hour after administration to the patient. In embodiments, microRNA treatment provides improvement in one or more symptoms of the disorder for more than 2 hours after administration to the patient. In embodiments, microRNA treatment provides improvement in one or more symptoms of the disorder for more than 3 hours after administration to the patient. In embodiments, microRNA treatment provides improvement in one or more symptoms of the disorder for more than 4 hours after administration to the patient. In embodiments, microRNA treatment provides improvement in one or more symptoms of the disorder for more than 6 hours after administration to the patient. In embodiments, microRNA treatment provides improvement in one or more symptoms of the disorder for more than 8, 10, 12, 14, 16, 18, 20, 22 or 24 hours after administration to the patient. In embodiments, improvement in at least one symptom for 12 hours after administration to the patient is provided in accordance with the present disclosure. In embodiments, microRNA treatment provides improvement of next day functioning of the patient. For example, the microRNA may provide improvement in one or more symptoms of the disorder for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, the methods described herein are effective to reduce, delay, or prevent one or more other clinical symptoms of Angelman Syndrome. For example, the effect in a patient of microRNA treatment in a target location of the central nervous system, including the brain, can be compared to an untreated patient, or the condition of the patient prior to treatment. In embodiments, a symptom, pharmacologic, and/or physiologic indicator is measured in a patient prior to treatment, and again one or more times after treatment is initiated. In embodiments, the control is a reference level, or average determined based on measuring the symptom, pharmacologic, or physiologic indicator in one or more patients that do not have the disease or condition to be treated (e.g., healthy patients). In embodiments, the amount of miR-145 and/or miR-92a in brain tissue prior to treatment is compared to the amount of miR-145 and/or miR-92a in brain tissue after treatment. In embodiments, the effect of the treatment is compared to a conventional treatment that is within the purview of those skilled in the art.

Effective treatment of Angelman Syndrome as disclosed herein may be established by showing reduction in the frequency or severity of symptoms (e.g., more than 10%, 20%, 30% 40% or 50%) after a period of time compared with baseline. For example, after a baseline period of 1 month, the patients having microRNA treatment may be randomly allocated a placebo as add-on therapy to standard therapies, during a double-blind period of 2 months. Primary outcome measurements may include the percentage of responders on a microRNA and on placebo, defined as having experienced at least a 10% to 50% reduction of symptoms during the second month of the double-blind period compared with baseline.

In embodiments, pharmaceutical compositions containing vectors, non-vector delivery vehicles, and/or the microRNA(s) may be provided with conventional release or modified release profiles. Pharmaceutical compositions may be prepared using a pharmaceutically acceptable "carrier" composed of materials that are considered safe and effective. The "carrier" includes all components present in the pharmaceutical formulation other than the active substance or ingredients. The term "carrier" includes, but is not limited to, diluents, binders, lubricants, disintegrants, fillers, and coating compositions. Those with skill in the art are familiar with such pharmaceutical carriers and methods of compounding pharmaceutical compositions using such carriers.

In embodiments, pharmaceutical compositions containing vectors, non-vector delivery vehicles, and/or the microRNA(s) are suitable for parenteral administration, including, e.g., intramuscular (i.m.), intravenous (i.v.), subcutaneous (s.c.), intraperitoneal (i.p.), or intrathecal (i.t.). Parenteral compositions must be sterile for administration by injection, infusion or implantation into the body and may be packaged in either single-dose or multi-dose containers. In embodiments, liquid pharmaceutical compositions for parenteral administration to a patient include an active substance, e.g., vectors, non-vector delivery vehicles, and/or the microRNA(s), in any of the respective amounts described above. In embodiments, the pharmaceutical compositions for parenteral administration are formulated as a total volume of about, e.g., 0.1 ml, 0.25 ml, 0.5 ml, 0.75 ml, 1 ml, 1.25 ml, 1.5 ml, 1.75 ml, 2 ml, 2.25 ml, 2.5 ml, 2.75 ml, 3 ml, 3.25 ml, 3.5 ml, 3.75 ml, 4 ml, 4.25 ml, 4.5 ml, 4.75 ml, 5 ml, 10 ml, 20 ml, 25 ml, 50 ml, 100 ml, 200 ml, 250 ml, or 500 ml. In embodiments, the volume of pharmaceutical compositions containing expression vectors are microliter amounts. For example, 0.1 microliters to 10 or more microliters can be injected. For example, 0.1, 0.2, 0.3, 0.4, 0.5, 0.6, 0.7, 0.8, 0.9, 1.0, 1.25, 1.5, 1.75, 2.0, 2.25, 2.5, 2.75, 3.0, 3.25, 3.5, 3.75, 4.0, 4.25, 4.5, 4.75, 5.0, 5.25, 5.5, 5.75, 6.0, 6.25, 6.5, 6.75, 7.0, 8.25, 8.5, 8.75, 9.0, 9.25, 9.5, 9.75, or 10 microliters. In embodiments, the compositions are contained in a micropipette, a bag, a glass vial, a plastic vial, or a bottle.

In embodiments, pharmaceutical compositions for parenteral administration include respective amounts described above. In embodiments, pharmaceutical compositions for parenteral administration include about 0.0001 mg to about 500 mg active substance, e.g., vectors, non-vector delivery vehicles, and/or the microRNA(s). In embodiments, pharmaceutical compositions for parenteral administration to a patient include an active substance, e.g., vectors, non-vector delivery vehicles, and/or the microRNA(s), at a respective concentration of about 0.001 mg/ml to about 500 mg/ml. In embodiments, the pharmaceutical composition for parenteral administration includes an active substance at a respective concentration of, e.g., about 0.005 mg/ml to about 50 mg/ml, about 0.01 mg/ml to about 50 mg/ml, about 0.1 mg/ml to about 10 mg/ml, about 0.05 mg/ml to about 25 mg/ml, about 0.05 mg/ml to about 10 mg/ml, about 0.05 mg/ml to about 5 mg/ml, or about 0.05 mg/ml to about 1 mg/ml. In embodiments, the pharmaceutical composition for parenteral administration includes an active substance at a respective concentration of, e.g., about 0.05 mg/ml to about 15 mg/ml, about 0.5 mg/ml to about 10 mg/ml, about 0.25 mg/ml to about 5 mg/ml, about 0.5 mg/ml to about 7 mg/ml, about 1 mg/ml to about 10 mg/ml, about 5 mg/ml to about 10 mg/ml, or about 5 mg/ml to about 15 mg/ml.

In embodiments, a pharmaceutical composition for parenteral administration is provided wherein the pharmaceutical composition is stable for at least six months. In embodiments, the pharmaceutical compositions for parenteral administration exhibit no more than about 5% decrease in active substance for at least, e.g., 3 months or 6 months. In embodiments, the amount of vector or non-vector vehicle, degrades at no more than about, e.g., 2.5%, 1%, 0.5% or 0.1%. In embodiments, the degradation is less than about, e.g., 5%, 2.5%, 1%, 0.5%, 0.25%, 0.1%, for at least six months.

In embodiments, pharmaceutical compositions for parenteral administration are provided wherein the pharmaceutical composition remains soluble. In embodiments, pharmaceutical compositions for parenteral administration are provided that are stable, soluble, local site compatible and/or ready-to-use. In embodiments, the pharmaceutical compositions herein are ready-to-use for direct administration to a patient in need thereof.

The pharmaceutical compositions for parenteral administration provided herein may include one or more excipients, e.g., solvents, solubility enhancers, suspending agents, buffering agents, isotonicity agents, stabilizers or antimicrobial preservatives. When used, the excipients of the parenteral compositions will not adversely affect the stability, bioavailability, safety, and/or efficacy of a vector, non-vector delivery vehicle, and/or the microRNA(s), used in the composition. Thus, parenteral compositions are provided wherein there is no incompatibility between any of the components of the dosage form.

In embodiments, parenteral compositions including vectors, non-vector delivery vehicles, and/or the microRNA(s) include a stabilizing amount of at least one excipient. For example, excipients may be selected from the group consisting of buffering agents, solubilizing agents, tonicity agents, antioxidants, chelating agents, antimicrobial agents, and preservative. One skilled in the art will appreciate that an excipient may have more than one function and be classified in one or more defined group.

In embodiments, parenteral compositions include a vector, non-vector delivery vehicle, and/or the microRNA(s) and an excipient wherein the excipient is present at a weight percent (w/v) of less than about, e.g., 10%, 5%, 2.5%, 1%, or 0.5%. In embodiments, the excipient is present at a weight percent between about, e.g., 1.0% to 10%, 10% to 25%, 15% to 35%, 0.5% to 5%, 0.001% to 1%, 0.01% to 1%, 0.1% to 1%, or 0.5% to 1%. In embodiments, the excipient is present at a weight percent between about, e.g., 0.001% to 1%, 0.01% to 1%, 1.0% to 5%, 10% to 15%, or 1% to 15%.

In embodiments, parenteral compositions may be administered as needed, e.g., once, twice, three, four, five, six or more times daily, or continuously depending on the patient's needs.

In embodiments, parenteral compositions of an active substance are provided, wherein the pH of the composition is between about 4.0 to about 8.0. In embodiments, the pH of the compositions is between, e.g., about 5.0 to about 8.0, about 6.0 to about 8.0, about 6.5 to about 8.0. In embodiments, the pH of the compositions is between, e.g., about 6.5 to about 7.5, about 7.0 to about 7.8, about 7.2 to about 7.8, or about 7.3 to about 7.6. In embodiments, the pH of the aqueous solution is, e.g., about 6.8, about 7.0, about 7.2, about 7.4, about 7.6, about 7.7, about 7.8, about 8.0, about 8.2, about 8.4, or about 8.6.

Unless defined otherwise, all technical and scientific terms used herein have the same meanings as commonly understood by one of skill in the art to which the disclosure herein belongs.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 10%, up to 5%, and/or up to 1% of a given value. Alternatively, particularly with respect to biological systems or processes, the term can mean within an order of magnitude, preferably within 5-fold, and more preferably within 2-fold, of a value.

"Improvement" refers to the treatment of Angelman Syndrome.

"Improvement in next day functioning" or "wherein there is improvement in next day functioning" refers to improvement after waking from an overnight sleep period wherein the beneficial effect of administration of microRNA therapy to a patient applies to at least one symptom of a syndrome or disorder herein and is discernable, either subjectively by a patient or objectively by an observer, for a period of time, e.g., 2 hours, 3 hours, 4 hours, 5 hours, 6 hours, 12 hours, 24 hours, etc. after waking.

"Treating", "treatment" or "treat" can refer to the following: alleviating or delaying the appearance of clinical symptoms of a disease or condition in a patient that may be afflicted with or predisposed to the disease or condition, but does not yet experience or display clinical or subclinical symptoms of the disease or condition. In certain embodiments, "treating", "treat" or "treatment" may refer to preventing the appearance of clinical symptoms of a disease or condition in a patient that may be afflicted with or predisposed to the disease or condition, but does not yet experience or display clinical or subclinical symptoms of the disease or condition. "Treating", "treat" or "treatment" also refers to inhibiting the disease or condition, e.g., arresting or reducing its development or at least one clinical or subclinical symptom thereof. "Treating", "treat" or "treatment" further refers to relieving the disease or condition, e.g., causing regression of the disease or condition or at least one of its clinical or subclinical symptoms. The benefit to a patient to be treated may be statistically significant, mathematically significant, or at least perceptible to the patient and/or the physician. Nonetheless, prophylactic (preventive) treatment and therapeutic (curative) treatment are two separate embodiments of the disclosure herein.

"Pharmaceutically acceptable" refers to molecular entities and compositions that are "generally regarded as safe", e.g., that are physiologically tolerable and do not typically produce an allergic or similar untoward reaction, such as gastric upset and the like, when administered to a human. In embodiments, this term refers to molecular entities and compositions approved by a regulatory agency of the federal or a state government, as the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

"Effective amount" or "therapeutically effective amount" can mean a dosage sufficient to alleviate one or more symptoms of a syndrome, disorder, disease, or condition being treated, or to otherwise provide a desired pharmacological and/or physiologic effect. "Effective amount" or "therapeutically effective amount" may be used interchangeably herein.

"Co-administered with", "administered in combination with", "a combination of" or "administered along with" may be used interchangeably and mean that two or more agents are administered in the course of therapy. The agents may be administered together at the same time or separately in spaced apart intervals. The agents may be administered in a single dosage form or in separate dosage forms.

"Patient in need thereof" may include individuals, e.g., mammals such as humans, canines, felines, porcines, rodents, etc., that have been diagnosed with Angelman Syndrome The methods may be provided to any individual including, e.g., wherein the patient is a neonate, infant, a pediatric patient (6 months to 12 years), an adolescent patient (age 12-18 years) or an adult (over 18 years). Patients include mammals. Such patients include those, for example, diagnosed with a genetic defect in the Ube3a gene.

"Prodrug" refers to a pharmacological substance (drug) that is administered to a patient in an inactive (or significantly less active) form. Once administered, the prodrug is metabolized in the body (in vivo) into a compound having the desired pharmacological activity.

"Analog" and "Derivative" may be used interchangeably and refer to a compound that possesses the same core as the parent compound, but may differ from the parent compound in bond order, the absence or presence of one or more atoms and/or groups of atoms, and combinations thereof. Enantiomers are examples of derivatives. The derivative can differ from the parent compound, for example, in one or more substituents present on the core, which may include one or more atoms, functional groups, or substructures. In general, a derivative can be imagined to be formed, at least theoretically, from the parent compound via chemical and/or physical processes.

The term "pharmaceutically acceptable salt", as used herein, refers to derivatives of the compounds defined herein, wherein the parent compound is modified by making acid or base salts thereof. Examples of pharmaceutically acceptable salts include, but are not limited to, nontoxic base addition salts with inorganic bases. Suitable inorganic bases such as alkali and alkaline earth metal bases include metallic cations such as sodium, potassium, magnesium, calcium and the like. The pharmaceutically acceptable salts can be synthesized from the parent compound by conventional chemical methods.

It should be understood that the examples and embodiments provided herein are exemplary examples embodiments. Those skilled in the art will envision various modifications of the examples and embodiments that are consistent with the scope of the disclosure herein. Such modifications are intended to be encompassed by the claims.

What is claimed is:

1. A method for treating Angelman Syndrome in a patient in need thereof, comprising administering to the patient a composition including a vector including a nucleic acid encoding microRNA-145, pri-miR145, pre-miR145, microRNA-92a, pri-miR-92a or pre-miRNA-92a, wherein said nucleic acid is operably linked to a promoter, wherein one or more symptoms of the Angelman Syndrome are improved and wherein the level of microRNA-145 and/or microRNA-92a is increased in the patient's brain.

2. The method according to claim 1, wherein the composition includes microRNA-145, pri-miR145, pre-miR145, microRNA-92a, pri-miR92a or pre-miR92a.

3. The method according to claim 1, wherein after the administering, expression of microRNA-145, pri-miR145, pre-miR145, microRNA-92a, pri-miR92a or pre-miR92a in the patient is associated with reduced symptoms of the Angelman Syndrome.

4. The method according to claim 1, wherein the promoter is selected from the group consisting of CAG promoter, CMV promoter, human synapsin 1 gene promoter (hSyn), dynorphin promoter, encephalin promoter and CaMKII promoter.

5. The method according to claim 1, wherein the vector includes at least one of a woodchuck post-transcriptional regulatory element (WPRE) and a fluorescence reporter cassette.

6. The method according to claim 1, wherein the vector is an adeno-associated virus (AAV) or a lentivirus.

7. The method according to claim 6, wherein the adeno-associated virus is AAV1, AAV2, AAV4, AAV5, AAV7, AAV8, AAV9 or AAVRec3.

8. The method according to claim 1, wherein the vector is delivered to a target location in the patient's brain.

9. The method according to claim 1, wherein the vector is administered via a route selected from the group consisting of oral, buccal, sublingual, rectal, topical, intranasal, vaginal and parenteral.

10. The method according to claim 1, wherein the composition includes a vector that is a non-viral vector.

11. The method of claim 10, wherein the non-viral vector is a liposome mediated delivery vector.

* * * * *